US008278110B2

(12) United States Patent
Ghobadi

(10) Patent No.: US 8,278,110 B2
(45) Date of Patent: *Oct. 2, 2012

(54) METHOD AND A BLOOD OXYGEN TESTER FOR DETECTING THE ARTERIAL OR VENOUS BLOOD

(76) Inventor: Ali Ghobadi, Anaheim, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/287,087

(22) Filed: Nov. 1, 2011

(65) Prior Publication Data

US 2012/0045791 A1    Feb. 23, 2012

Related U.S. Application Data

(63) Continuation of application No. 12/408,238, filed on Mar. 20, 2009, now Pat. No. 8,080,424.

(51) Int. Cl.
*G01N 33/50* (2006.01)
*G01N 33/80* (2006.01)
*A61B 5/157* (2006.01)

(52) U.S. Cl. ............ 436/68; 436/63; 436/164; 436/169; 422/400; 422/402; 422/420; 422/68.1; 422/82.01; 422/82.04; 422/82.13; 435/2; 600/584

(58) Field of Classification Search ............ 436/63, 436/68, 164, 165, 169, 148; 422/400, 401, 422/402, 420, 430, 68.1, 82.01, 82.04, 82.13, 83, 86, 87, 88, 98; 435/2; 600/573, 576, 600/584; 604/503

See application file for complete search history.

(56) References Cited

U.S. PATENT DOCUMENTS

| | | | | |
|---|---|---|---|---|
| 3,785,367 A | * | 1/1974 | Fortin et al. ............... | 600/576 |
| 4,197,853 A | * | 4/1980 | Parker ...................... | 600/354 |
| 6,066,243 A | * | 5/2000 | Anderson et al. ......... | 422/82.01 |
| 6,217,558 B1 | * | 4/2001 | Zadini et al. .............. | 604/187 |
| 6,605,471 B1 | * | 8/2003 | Lundsgaard et al. ..... | 436/165 |
| 8,080,424 B2 | * | 12/2011 | Ghobadi .................... | 436/68 |
| 2007/0265550 A1 | * | 11/2007 | Choi et al. ................. | 600/584 |

* cited by examiner

*Primary Examiner* — Maureen Wallenhorst
(74) *Attorney, Agent, or Firm* — The Patel Law Firm, P.C.; Natu J. Patel

(57) ABSTRACT

A method and a blood oxygen tester for determining whether a blood sample is arterial or venous blood are disclosed. A blood oxygen tester for determining whether a blood sample is arterial or venous blood includes a housing and a blood sample receptacle defined by the housing. A blood oxygen sensor is in communication with the blood sample receptacle and a test result indicator is in communication with the blood oxygen sensor. The indicator is responsive to the blood oxygen sensor for indicating whether a tested blood sample is arterial blood or venous blood.

18 Claims, 3 Drawing Sheets

METHOD AND A BLOOD OXYGEN TESTER FOR DETECTING THE ARTERIAL OR VENOUS BLOOD

CROSS REFERENCE TO RELATED APPLICATION

This utility patent application is a continuation of U.S. patent application entitled "METHOD AND A BLOOD OXYGEN TESTER FOR DETECTING THE ARTERIAL OR VENOUS BLOOD" by the same inventor, Ser. No. 12/408,238, filed Mar. 20, 2009, now U.S Pat. No. 8,080,424, issued on Dec. 20, 2011, the disclosure of the aforementioned application is being incorporated herein in its entirety by reference.

COPYRIGHT NOTICE

Portions of the disclosure of this patent document may contain material that is subject to copyright and/or mask work protection. The copyright and/or mask work owner has no objection to the facsimile reproduction by anyone of the patent document or the patent disclosure, as it appears in the Patent and Trademark Office patent file or records, but otherwise reserves all copyright and/or mask work rights whatsoever.

BACKGROUND OF THE INVENTION

1. Field of the Invention

The present invention relates to medical devices in general and more particularly to a portable device and a method for determining whether the blood sample extracted from the patient's body is arterial or venous.

2. Discussion of the Related Art

People who are extremely ill or injured are often admitted for medical care through a hospital's emergency room (ER). In administering emergency care medicine in an ER, time is a very valuable commodity. The patient's well being and even life may depend on rapid administration of proper medical care. Central Venous Catheters, also known as "Central lines", are most commonly used for administration of IV fluids, antibiotics, blood transfusions, nutritional supplements, or medications used to support and improve blood pressure, which are optimally delivered through central lines. These catheters are also important for checking serial blood tests and monitoring the fluid and hydration status of the patient. In emergency and critical care medicine, these catheters are vital for resuscitation, monitoring, and optimal management of critically ill patients.

Central line catheters are long and large bore catheters and are designed to be inserted into veins. Veins are low pressured and return blood from organs and tissues to the heart and arteries are high pressured and carry oxygenated blood to organs and bodily tissues. Central lines are inserted into the large veins of the body, typically one of three large veins such as the internal jugular vein (located in the neck), the subclavian vein (located in the chest), or the femoral vein (located in the groin). These large veins run next to major arteries; the internal jugular runs alongside the carotid artery in the neck, the subclavian vein runs alongside the subclavian artery in the chest, and the femoral vein runs alongside the femoral artery in the groin area.

To accomplish the insertion of a central line, the patient is properly positioned and the insertion area is sterilized. The medical professional uses either anatomic landmarks or ultrasound to identify the location of the vein for insertion. The area is anesthetized and an 'introducer needle' connected to a syringe is advanced until the tip of the needle is in the desired vein. Placement of the needle in the vein is confirmed by aspiration of blood into the syringe. A guide wire and a dilator tube are then introduced to guide the catheter in place at which time the catheter is sutured in place. Appropriate positioning of the catheter is confirmed by taking a chest x-ray.

Because of the proximity of the vein to the corresponding artery, a major risk during the insertion of central lines is accidental arterial cannulation, or the advancement and placement of the catheter into a large artery instead of the vein. Arterial cannulation has potential catastrophic implications including hemothorax (bleeding into the chest cavity), carotid, subclavian, or femoral artery injury, stroke, and even death. Thus, ER personnel are intent on distinguishing arterial versus venous blood prior to cannulating with the dilator and inserting and suturing the catheter. Current methods of distinguishing venous from arterial blood are inaccurate, unreliable, or impractical.

The most common method of distinguishing venous from arterial blood during catheter placement is visual analysis. Arterial blood is classically a brighter red and more pulsatile in comparison to venous blood. However, these characteristics are very subjective and thus unreliable. The color of a patient's blood sample can be incorrectly interpreted depending on a variety of factors such as the patient's blood oxygenation, past medical history, operator experience, and even the ambient lighting in the room where the procedure is performed. Further, ill patients receiving central lines often have low blood pressure who would not exhibit classic pulsatile arterial blood flow to distinguish arterial blood from venous blood.

Another method is the use of blood gas analysis. In this method, a sample of blood is placed in a machine and after analysis the machine displays the amount of oxygenation. While accurate, blood gas analysis is not easily available and is time consuming. In many hospitals, this test is only performed in a laboratory and can take five minutes or more to obtain results. If the patient is in need of emergency care, proper care often requires more immediate action than available when the care givers must wait on machine analysis.

Pressure waveform monitoring is also used to determine the source of a blood sample. However, this method is limited because most cardiac monitors do not have this option available. Also, this method is time consuming to set up and requires additional people to complete the process. Since this method depends on the pressure of the blood sample to distinguish between arterial and venous blood, low blood pressure in some sick patients can cause unreliable results.

Another method to aid in the placement of the catheter is the use of ultrasound. This method has been shown to reduce patient discomfort and the number of arterial sticks. Because of the high pliancy of vessel walls, veins tent and collapse when the central line is being placed. Even under ultrasound guidance, the medical professional can puncture through the vein resulting in arterial insertion. Therefore, ultrasound guidance does not offer the reliability desired to readily distinguish arterial blood from venous blood.

Although there are various studies published in medical journals that provide a comparison of arterial and venous blood gas values before, during, and after the operation of the patient, none of that information is utilized in developing a method or a device to place central line kits efficiently, safely and accurately within the patient's body. Thus what is desired is a testing device that can readily distinguish between arterial and venous blood in minimal time and at the patient's bedside quickly and accurately to facilitate the placement of central line kits in an emergency situation.

SUMMARY OF THE INVENTION

The present invention is directed to a blood oxygen tester that satisfies the need for quick and reliable testing of blood for determining whether a sample is arterial or venous blood at a patient's bedside. The blood oxygen tester comprises a housing and a blood sample receptacle defined by the housing. A blood oxygen sensor is in communication with the blood sample receptacle and a test result indicator is in communication with the blood oxygen sensor. The indicator is responsive to the blood oxygen sensor for indicating whether a tested blood sample is arterial blood or venous blood.

Another aspect of the present invention is a blood oxygen tester for determining whether a blood sample is arterial or venous. The blood oxygen tester comprises a housing having a volume of less than fifty cubic centimeters and defining a blood sample receptacle for receiving a blood sample. A blood oxygen sensor in the housing includes a reaction strip responsive to an oxygen saturation level in the blood sample. The housing further defines a test result indicator in communication with the blood oxygen sensor and is responsive to the blood oxygen sensor. The indicator displays a first color when the tested blood sample is venous blood and a second color when the tested blood sample is arterial blood.

In another aspect of the present invention is a method for determining whether a patient's blood sample is venous or arterial blood utilizing a blood oxygen tester. The method includes steps of preparing a site on the patient's body to withdraw a blood sample, inserting a needle through the site to withdraw the blood sample, aspirating the blood sample, and depositing the blood sample in a receptacle of a blood oxygen tester. The blood oxygen tester includes a blood oxygen sensor comprising a reaction strip responsive to a certain characteristics of the blood. The method further includes viewing the results of the blood sample to determine whether the blood withdrawn is arterial or venous blood. If the withdrawn blood is the venous blood, the medical professional completes the insertion of a central line. If it is arterial blood, the medical professional withdraws the needle and restarts the procedure. The reaction strip is designed to detect the oxygen saturation level or partial pressure oxygen (pO2) to identify whether the blood withdrawn is arterial or venous.

In yet another of the present invention is a method of testing a patient's blood sample at the patient's bedside to determine whether the blood is venous or arterial blood. The method comprises the steps of preparing a site on the patient's body for insertion of an introducer needle. An introducer needle is coupled with a syringe. The introducer needle is inserted through the patient's anatomy and into a vein. A sample of blood is aspirated into the syringe. The syringe is removed from the introducer needle, and the blood sample is deposited in a blood sample receptacle of a blood oxygen tester at the patient's bedside. The blood sample is allowed to contact a blood oxygen sensor in the blood oxygen tester comprising a reaction strip responsive to an oxygen saturation level in the blood sample. A test result indicator responsive to the blood oxygen sensor is viewed and indicates a first color when the tested blood sample is venous blood and indicates a second color when the tested blood sample is arterial blood.

These and other features, aspects, and advantages of the invention will be further understood and appreciated by those skilled in the art by reference to the following written specification, claims and appended drawings.

BRIEF DESCRIPTION OF THE DRAWINGS

To the accomplishment of the above and related objectives, this invention may be embodied in the form illustrated in the accompanying drawings, attention being called to the fact, however, that the drawings are illustrative only, and that changes may be made in the specific construction and method illustrated.

Like reference numerals refer to like parts throughout the several views of the drawings.

DETAILED DESCRIPTION OF THE INVENTION

Figure 2:
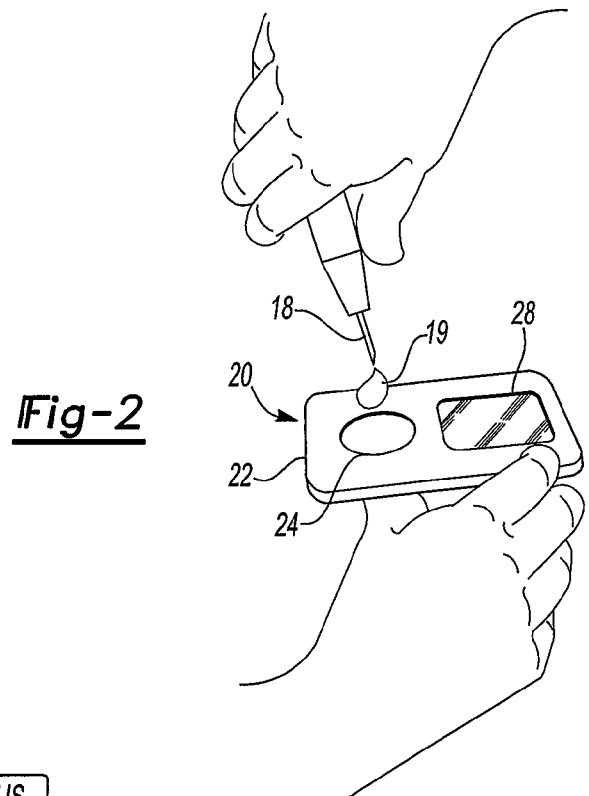
FIG. 2 is a perspective view of a medical professional administering a blood sample to a blood oxygen tester embodying the present invention.

For purposes of description herein, the terms "upper", "lower", "left", "rear", "right", "front", "vertical", "horizontal", and derivatives thereof shall relate to the invention as oriented in FIG. 2. However, one will understand that the invention may assume various alternative orientations and step sequences, except where expressly specified to the contrary. Therefore, the specific devices and processes illustrated in the attached drawings, and described in the following specification, are simply various embodiments of the inventive concepts defined in the appended claims. Hence, specific dimensions and other physical characteristics relating to the embodiments disclosed herein are not to be considered as limiting, unless the claims expressly state otherwise.

Figure 1:
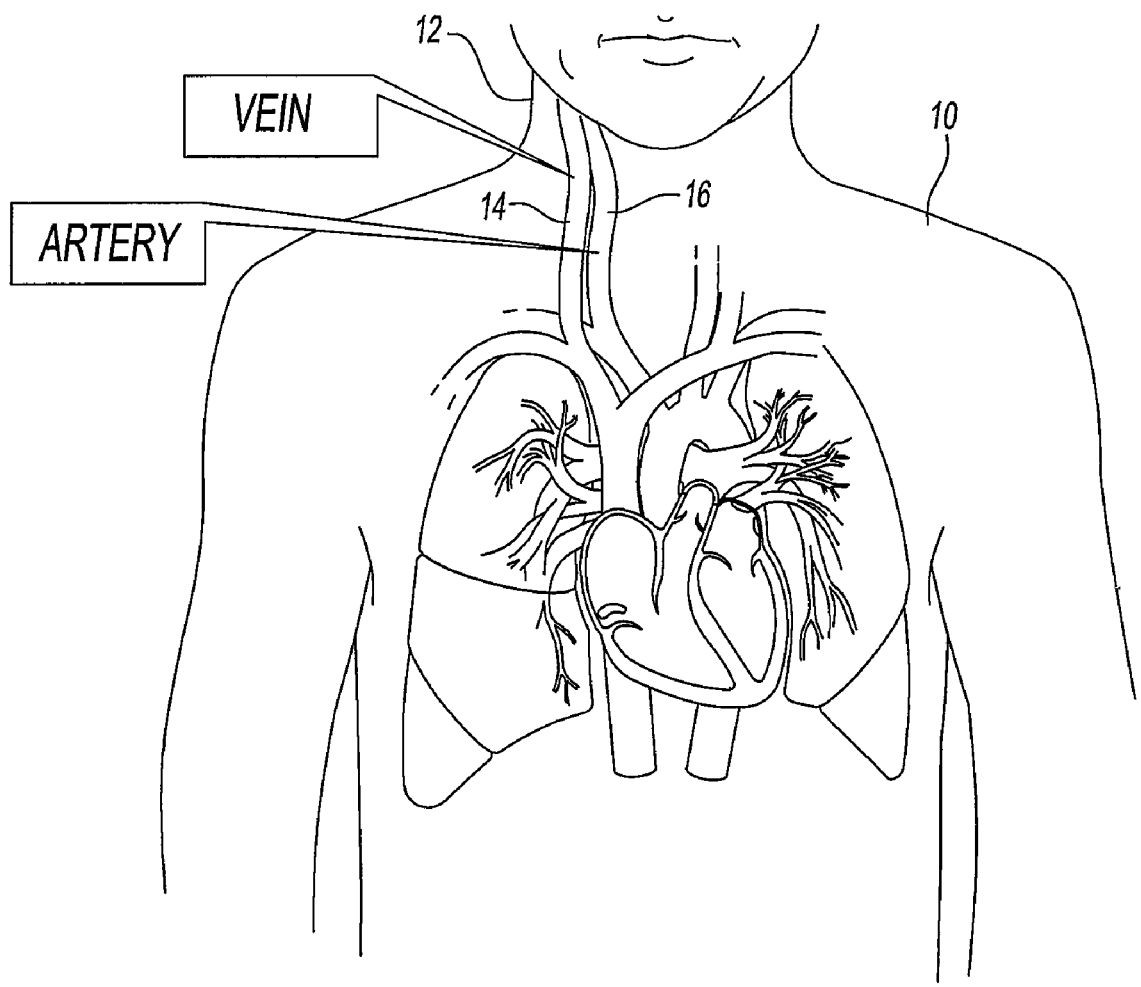
FIG. 1 is a view of a portion of a person's cardiovascular system illustrating the proximal location of a person's veins and arteries.

Turning to the drawings, FIG. 1 shows a medical patient 10 requiring the insertion of a central line catheter into a jugular vein 14 of a patient's neck 12. A blood sample 19 must be extracted for testing by an oxygen blood tester 20 to ensure that the catheter is being introduced to jugular vein 14 and not a carotid artery 16 located alongside jugular vein 14.

Figure 3:
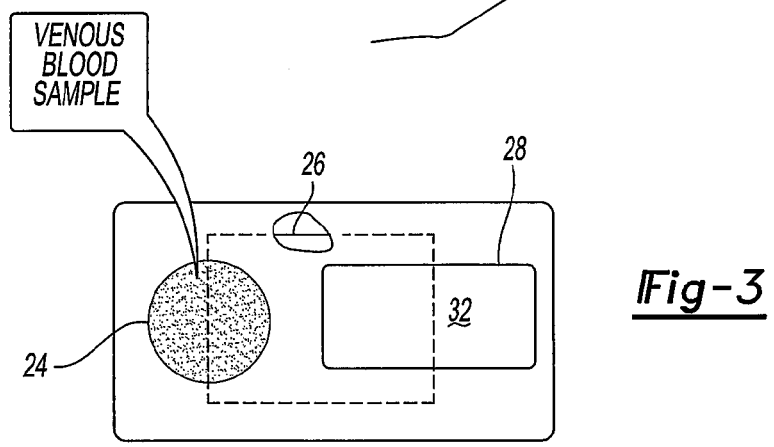
FIG. 3 is a plan view of the blood oxygen tester illustrating test results from a venous blood sample.
Figure 4:
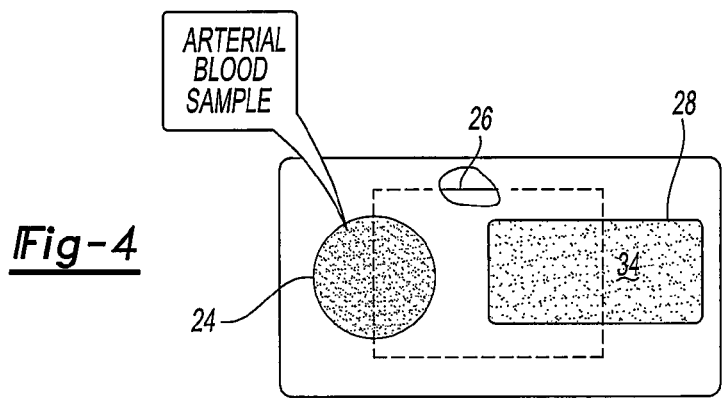
FIG. 4 is a plan view of the blood oxygen tester illustrating test results from an arterial blood sample.

FIGS. 2-4 illustrate oxygen blood tester 20 which is one embodiment of the present invention and illustrates its various components. In this embodiment, blood tester 20 includes a housing 22 that defines a blood sample receptacle 24 for receiving a blood sample and a test result indicator 28 for displaying the result of a blood test performed with blood tester 20. Housing 22 is of a sufficiently small size so that tester 20 can be included in pre-existing central line kits that are commercially available (not shown). Such central line kits are readily stocked for use in medical facilities, the contents of which are designed for one-time use. Likewise, blood tester 20 in one embodiment is anticipated to also be a one-time use item. Housing 22 has a volume of less than 100 cubic centimeters and ideally less than 50 cubic centimeters for convenient use by a medical professional. In one embodiment, the housing may be five to ten centimeters in length, three to five centimeters in width, and less than one centimeter in height. Blood tester 20 also encloses a blood oxygen sensor 26 within housing 22. Blood oxygen sensor 26 is in communication with blood sample receptacle 24 and with test result indicator 28.

In one embodiment, the difference between the oxygen saturation of venous and arterial blood can be used to determine the proper placement of the central line. In the human cardiovascular system, blood is circulated by the heart through the lungs where the blood is oxygenated. Oxygenated (arterial) blood is pumped by the heart through arteries to the rest of the body where organs and tissue extract oxygen from the blood. Arterial blood being freshly oxygenated has a normal oxygen saturation above ninety-five percent and, in most patients, is near one hundred percent. Once the oxygenated blood reaches the organs and various tissue of the body, at least a portion of the oxygen is absorbed by the organs and tissues to create energy. Venous (de-oxygenated) blood is then carried back to the heart by veins to again to be oxygenated by the lungs. Venous blood has a normal oxygen saturation that typically has a maximum of seventy-five percent oxygen saturation since oxygen has been extracted from the blood by organs and tissue. Consequently, the oxygen saturation of venous blood is generally less than seventy-five percent whereas the oxygen saturation of arterial blood is almost always above ninety to ninety-five percent.

In this embodiment, blood oxygen sensor 26 is a reaction strip that is responsive to the oxygen saturation level in a blood sample. The reaction strip in sensing an oxygen saturation level corresponding to venous blood will provide a first indication in test result indicator 28 and in sensing an oxygen saturation level corresponding to arterial blood will provide a second indication distinct from the first indication in test result indicator 28. The reaction strip can be impregnated or coated with a reactive dye such that the reactive dye assumes a first color 32 (FIG. 3) for display in test result indicator 28 when exposed to venous blood in receptacle 24 and assumes a second color 34 (FIG. 4) for display in test result indicator 28 when exposed to arterial blood in receptacle 24. The reactive dye can have a color change threshold corresponding to an oxygen saturation level of eighty percent, or in another embodiment, an oxygen saturation level of ninety percent.

In another embodiment, the $pO_2$ differential between arterial and venous blood can also be used to determine the proper placement of the central line. Arterial or venous blood can also be distinguished by its partial pressure of oxygen ($pO_2$). Before operation, arterial blood will typically have a $pO_2$ level range of approximately 70-100 mmHg (millimeter of mercury) while venous blood will typically have a $pO_2$ level range of approximately 30-40 mmHg. Thus, the $pO_2$ differential between arterial and venous blood is significant and provides a reliable indication of which blood sample has been drawn from the patient.

In this embodiment, blood oxygen tester 20 can include sensor 26 that is reactive to the partial pressure of oxygen (pO2) in the blood sample. Sensor 26 can include a known micro-dissolved oxygen electrode that is reactive to a partial pressure of oxygen in the blood sample. Alternatively, sensor 26 can be an electro-chemical sensor that is reactive to the partial pressure of oxygen in the blood sample.

In use, blood oxygen tester 20 can be included with a central line catheter kit to aid the medical professional in correct placement of the catheter in one of the patient's major veins (i.e. jugular vein, subclavian vein, femoral vein). The patient is prepared for the procedure by placing the patient's body in a desired orientation for the procedure. The medical professional can then take appropriate sterile measures such as wearing a sterile gown, gloves, and mask and sterilizing the body site (i.e. neck 12) where the procedure is to be performed. The medical professional then identifies the location of the desired vein (i.e. jugular vein 14) by using anatomic landmarks or by an ultrasound device. The procedure site can then be anesthetized. An introducer needle is coupled with a syringe 18 and the needle is then advanced through the patient's skin and tissue into jugular vein 14. The medical professional aspirates the syringe 18 while advancing the needle until blood is aspirated into syringe 18. Syringe 18 is removed while the needle remains in place in the vein, and a sample 19 of the blood is placed in receptacle 24 of blood oxygen tester 20.

Once blood sample 19 has been placed in receptacle 24, the medical professional waits a prescribed period of time (typically a few seconds) to allow the reactive strip or sensor 26 to react to the oxygen saturation level of blood sample 19. After the expiration of the prescribed time, the result of the test is read from test result indicator 28. If the blood sample is venous blood, test result indicator 28 will display first color 32, and if the blood sample is arterial blood, test result indicator 28 will display second color 34. In this manner, the medical professional will quickly know whether the introducer needle has been placed in the desired vein or has been introduced in an undesired artery. If test result indicator 28 displays second color 32 indicating arterial blood, the introducer needle can be repositioned to the vein. A second blood sample is then obtained and tested on a new blood oxygen tester 20.

Once the medical professional verifies that the introducer needle is correctly placed in desired vein 14, a guide wire is advanced through the introducer needle and into the vein. The introducer needle is then removed and a dilator tube is advanced over the guide wire into the vein to open a tract for the catheter and then immediately removed. The catheter is then placed over the wire into the vein and the guide wire is removed. The ports are then flushed and sutured in place. Correct placement of the catheter can then be confirmed by taking an x-ray of the area at the procedure site.

Figure 5:
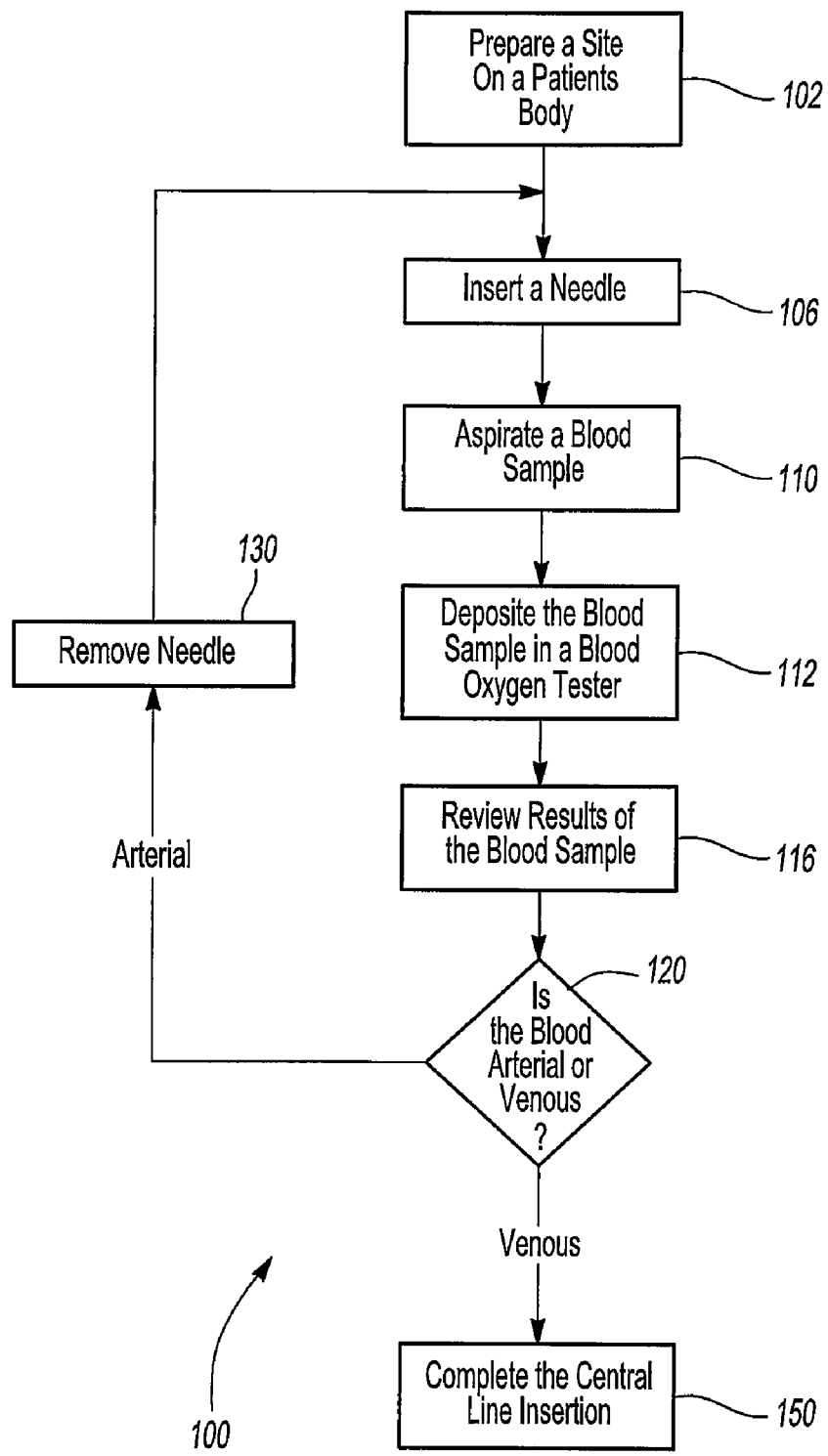
FIG. 5 is a flow chart illustrating a method of detecting a patient's blood sample to determine whether the blood is venous or arterial.

A method 100 for using blood oxygen tester 20 is shown in FIG. 5. In block 102, the medical professional prepares a site on a patient's body for insertion of a central line. The preparation can include such procedures as shaving the patient's skin, sterilizing the skin surface, adding a sterile drape, etc. Once the site has been prepared, in block 106 the medical professional inserts a needle through the patient's skin into a desired vein. Once the needle has been inserted into the vein, a blood sample is aspirated through the needle in block 110. Then, in block 112 the sample is deposited in blood oxygen tester 20 and allowed to interact with sensor 26.

Once the blood sample has interacted with sensor 26, the medical professional, in block 116, reads the results of the blood sample as displayed by indicator 28. In block 120, and in response to the display of indicator 28, the medical professional determines if the blood sample is arterial or venous blood. If the medical professional determines that the blood sample is arterial, the needle is removed in block 130 and the method returns to block 106 for reinsertion of the needle in a desired vein. Blocks 106 through 120 are then repeated until, as a result of the indication of display 28, the medical professional determines that the blood sample is venous. The method then proceeds to block 150. In block 150, the medical professional completes the insertion of the central line with the knowledge that the line is being inserted into a patient's vein and not into an artery.

The above description is considered that of representative embodiments only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the doctrine of equivalents.

I claim:

1. A blood oxygen tester for determining whether a blood sample is arterial or venous, said blood oxygen tester comprising:
   a housing;
   a blood sample receptacle defined by said housing and having an area for depositing a blood sample;
   a blood oxygen sensor within said area in the blood sample receptacle, said blood oxygen sensor reactive to a partial pressure of oxygen (pO2) in the blood sample; and
   a test result indicator defined by said housing and in communication with said blood oxygen sensor, said indicator responsive to said blood oxygen sensor's reaction to the partial pressure of oxygen (pO2) in the deposited blood sample displaying a first color when the blood sample is arterial blood and indicating a second color when the blood sample is venous blood.

2. The blood oxygen tester according to claim 1, wherein said housing has a volume of less than one hundred cubic centimeters.

3. The blood oxygen tester according to claim 1, wherein said housing has a volume of less than fifty cubic centimeters.

4. The blood oxygen tester according to claim 1, wherein said blood oxygen sensor reacts to a partial pressure of oxygen (pO2) greater than seventy mmHg in the blood sample.

5. The blood oxygen tester according to claim 4, wherein said test result indicator displaying the first color based on said blood oxygen sensor's reaction to the partial pressure of oxygen (pO2) greater than seventy mmHg.

6. The blood oxygen tester according to claim 1, wherein said blood oxygen sensor reacts to a partial pressure of oxygen (pO2) less than forty mmHg in the blood sample.

7. The blood oxygen tester according to claim 6, wherein said test result indicator displaying the second color based on said blood oxygen sensor's reaction to the partial pressure of oxygen (pO2) less than forty mmHg in the blood sample.

8. A method for determining whether a patient's blood sample is venous or arterial blood utilizing a blood oxygen tester, said method comprising:
   preparing a site on the patient's body to withdraw a blood sample;
   inserting a needle through the site to withdraw the blood sample;
   aspirating the blood sample;
   depositing the aspirated blood sample in a receptacle of a blood oxygen tester, said receptacle includes a blood oxygen sensor reactive to a partial pressure of oxygen (pO2) in the blood; and
   viewing a color on a test result indicator to determine whether the blood withdrawn is arterial or venous blood, said indicator displaying the color responsive to said blood oxygen sensor's reaction to the partial pressure of oxygen (pO2) in the deposited blood sample.

9. The method according to claim 8, wherein said test result indicator displaying a first color when the blood sample is venous blood and indicating a second color when the blood sample is arterial blood.

10. The method according to claim 8, wherein said blood oxygen sensor includes a micro dissolved oxygen electrode reactive to the partial pressure of oxygen in the blood sample.

11. The method according to claim 8, wherein said blood oxygen sensor is an electrochemical sensor reactive to the partial pressure of oxygen in the blood sample.

12. The method according to claim 8, wherein said blood oxygen sensor comprises a reaction strip reactive to the partial pressure of oxygen (pO2).

13. A blood oxygen tester comprising:
   a blood oxygen sensor reactive to a partial pressure of oxygen (pO2), wherein said blood oxygen sensor includes a micro dissolved oxygen electrode reactive to the partial pressure of oxygen in a blood sample; and
   a test result indicator in communication with said blood oxygen sensor, said indicator responsive to said blood oxygen sensor's reaction to the partial pressure of oxygen (pO2) in a blood sample indicating whether the blood sample is arterial blood or venous blood.

14. A blood oxygen tester comprising:
   a blood oxygen sensor reactive to a partial pressure of oxygen (pO2), wherein said blood oxygen sensor is an electrochemical sensor reactive to the partial pressure of oxygen in a blood sample; and
   a test result indicator in communication with said blood oxygen sensor, said indicator responsive to said blood oxygen sensor's reaction to the partial pressure of oxygen (pO2) in a blood sample indicating whether the blood sample is arterial blood or venous blood.

15. The blood oxygen tester of claim 14, wherein said indicator indicating a first color if the blood sample is arterial blood or a second color if the blood sample is venous blood.

16. A blood oxygen tester comprising:
   a housing having a volume of less than fifty cubic centimeters;
   a blood sample receptacle defined by said housing for depositing a blood sample;
   a blood oxygen sensor within said receptacle in said housing, said blood oxygen sensor reactive to a partial pressure of oxygen (pO2) in the deposited blood sample; and
   a test result indicator defined by said housing and in communication with said blood oxygen sensor, said indicator responsive to said blood oxygen sensor's reaction to the partial pressure of oxygen displaying a first color when the tested blood sample is venous blood and indicating a second color when the tested blood sample is arterial blood.

17. The blood oxygen tester of claim 16, wherein said blood oxygen sensor includes a micro dissolved oxygen electrode reactive to the partial pressure of oxygen in the blood sample.

18. The blood oxygen tester of claim 16, wherein said blood oxygen sensor is an electrochemical sensor reactive to the partial pressure of oxygen in the blood sample.

* * * * *